(12) United States Patent
Speidel et al.

(10) Patent No.: US 12,133,754 B2
(45) Date of Patent: Nov. 5, 2024

(54) SYSTEM AND METHOD FOR SIMULTANEOUS ACQUISITION OF CONTRAST DYNAMICS AND ANATOMICAL IMAGES

(71) Applicant: WISCONSIN ALUMNI RESEARCH FOUNDATION, Madison, WI (US)

(72) Inventors: Michael Speidel, Madison, WI (US); Paul Laeseke, Madison, WI (US); Carson Hoffman, Madison, WI (US); Joseph Whitehead, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 230 days.

(21) Appl. No.: 17/721,697

(22) Filed: Apr. 15, 2022

(65) Prior Publication Data

US 2023/0329658 A1 Oct. 19, 2023

(51) Int. Cl.
*A61B 6/50* (2024.01)
*A61B 6/00* (2024.01)
*A61B 6/03* (2006.01)
*A61B 6/40* (2024.01)
(Continued)

(52) U.S. Cl.
CPC .............. *A61B 6/504* (2013.01); *A61B 6/03* (2013.01); *A61B 6/405* (2013.01); *A61B 6/481* (2013.01); *A61B 6/542* (2013.01); *G06T 7/0012* (2013.01); *G06T 7/254* (2017.01); *A61B 6/4441* (2013.01);
(Continued)

(58) Field of Classification Search
CPC ........... A61B 6/504; A61B 6/03; A61B 6/405; A61B 6/481; A61B 6/542; A61B 6/4441; A61B 6/032; A61B 6/5235; G06T 7/0012; G06T 7/254; G06T 2207/10072; G06T 2207/20224; G06T 2207/30101;
(Continued)

(56) References Cited

U.S. PATENT DOCUMENTS 7,826,587 B1 * 11/2010 Langan ................. A61B 6/482
378/20
2003/0195416 A1 * 10/2003 Toth ....................... A61B 6/405
378/4
(Continued)

OTHER PUBLICATIONS

Lira, Diego, et al. "Tube potential and CT radiation dose optimization." American journal of roentgenology 204.1 (2015): W4-W10. (Year: 2015).*
(Continued)

*Primary Examiner* — Sean D Mattson
(74) *Attorney, Agent, or Firm* — Quarles & Brady, LLP

(57) ABSTRACT

A system and method are provided for creating both angiographic images of a subject and dynamic images of the subject from imaging data acquired during an imaging acquisition. The method includes operating an imaging system to perform an imaging acquisition by delivering interspersed doses of high doses of the ionizing radiation and low doses of the ionizing radiation, wherein more low doses of the ionizing radiation are delivered than high doses of ionizing radiation during the imaging acquisition to thereby acquire the imaging data with a high frame rate of low dose data and a low frame rate of high dose data. The method also includes generating at least volumetric angiographic images of the subject and dynamic images of the subject from the imaging data.

18 Claims, 7 Drawing Sheets

(51) Int. Cl.
  *G06T 7/00* (2017.01)
  *G06T 7/254* (2017.01)
(52) U.S. Cl.
  CPC .............. *G06T 2207/10072* (2013.01); *G06T 2207/20224* (2013.01); *G06T 2207/30101* (2013.01)
(58) Field of Classification Search
  CPC ........ G16H 30/20; G16H 30/40; G16H 40/63; G16H 40/67
  See application file for complete search history.

(56) References Cited

U.S. PATENT DOCUMENTS

| | | | | |
|---|---|---|---|---|
| 2009/0092219 | A1* | 4/2009 | Wu | A61B 6/4241 378/5 |
| 2013/0170615 | A1* | 7/2013 | Wei | H04N 25/63 250/371 |
| 2017/0249758 | A1* | 8/2017 | Mistretta | A61B 6/504 |
| 2019/0329069 | A1 | 10/2019 | Blankenbecler | |
| 2020/0043573 | A1 | 2/2020 | Fält et al. | |
| 2020/0155103 | A1* | 5/2020 | Mistretta | A61B 6/5235 |

OTHER PUBLICATIONS

International Search Report and Written Opinion for corresponding Application No. PCT/US/2023015298, mailed Jun. 14, 2023.

\* cited by examiner

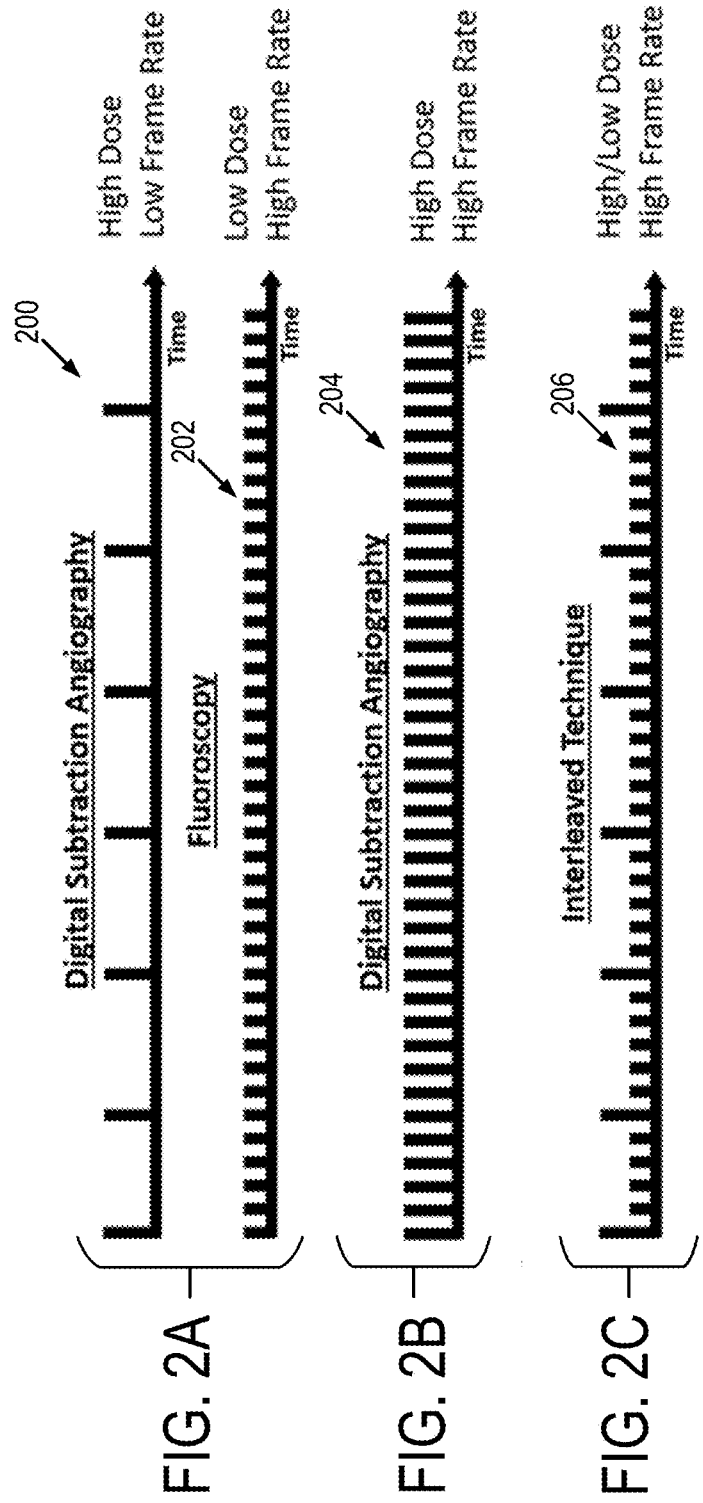

SYSTEM AND METHOD FOR SIMULTANEOUS ACQUISITION OF CONTRAST DYNAMICS AND ANATOMICAL IMAGES

STATEMENT REGARDING FEDERALLY SPONSORED RESEARCH

N/A

BACKGROUND

The present disclosure relates to systems and methods for medical image data acquisition and/or reconstruction. More particularly, systems and methods are provided for producing medical images that can include multiple types of images acquired simultaneously or during the same acquisition process, such as angiographic images and hemodynamic images.

Clinical outcomes for many conditions are directly correlated to the amount of accurate information that is available to a clinician and the speed with which the information or updated information can be provided. The ability to successfully diagnose and treat vascular conditions is highly dependent upon detailed and accurate information being available to clinicians. Furthermore, the dependence upon and availability of accurate information is important in both the diagnostic and treatment phases. Medical imaging is one of the key clinically-available sources of the information necessary to diagnose and treat patients.

Conventional 2D projection x-ray imaging, generally two-dimensional (2D) digital subtraction angiography (DSA), uses an injected contrast agent to visualize the flow of blood, and can be performed in the interventional suite. In addition to 2D DSA, some have developed three-dimensional (3D) DSA. More recently, time-resolved or "4D" DSA technology can be coupled with separate flow information to provide time-resolved imaging of contrast agent flow through a 3D vascular tree.

Unfortunately, though clinicians agree that the information provided by these and similar techniques is highly-informative and can produce better clinical outcomes, the adoption of such techniques is limited by dose considerations. That is, x-ray imaging uses ionizing radiation, which is subject to limits to protect patients from the well-known risks presented by overexposure to ionizing radiation. Even beyond these limits, clinicians seek to limit exposure to ionizing radiation when possible. The US Food and Drug Administration (FDA), for example, has had a long-standing "Initiative to Reduce Unnecessary Radiation Exposure from Medical Imaging." Thus, clinicians are constantly weighing the benefits of the information provided by imaging, such as provided by DSA, against the desire to reduce patient exposure to radiation dose.

With this in mind, though physiological information such as blood velocity can be highly informative to guiding clinical procedures and can be available via DSA, such information requires a high frame rate (e.g., 30 frames per second) because the blood moves at a speed that can be visualized with DSA at or above 30 frames per second. Unfortunately, in many cases, clinicians are forced to determine that the radiation dose required to acquire 30 frames every second is too great. Thus, the clinicians are forced to conduct the interventional procedure without information on blood velocity, which would otherwise be highly informative in a wide-variety of procedures, such as the placement of endovascular coils, embolic particles, stents, or the like.

Therefore, it would be desirable to have systems and methods for producing the anatomical images necessary to guide interventional procedures (e.g., to generate reference vascular images or roadmaps), while also providing physiological or dynamic information, but while the keeping the radiation dose within acceptable ranges to enable the information to be utilized in a wider variety of clinical procedures.

SUMMARY

The present disclosure overcomes the aforementioned drawbacks by providing systems and methods for generating diagnostic quality angiographic images and flow kinetics or velocity at a reduced radiation dose relative to traditional imaging procedures, such as DSA and fluoroscopy. In one non-limiting example, diagnostic quality angiographic images and flow kinetics or velocity can be generated using the systems and methods of the present disclosure in a single scan, while reducing patient radiation dose and contrast media load compared to traditional imaging procedures, such as DSA. In accordance with one non-limiting aspect of the disclosure, x-ray tube parameters (kV, mA, ms, and the like) may be controlled or modulated on a frame-by-frame basis during acquisition of a sequence of x-ray images to produce an interleaved sequence of high and low dose frames. In this non-limiting example, an interleaved sequence may be designed such that the overall frame rate is desirably high for a given clinical purpose, such as 30 frames per second for tracking hemodynamics, but such that the high-dose frames are generated at a low rate and the remaining frames are low dose. In one non-limiting example, the overall acquisition may acquire 30 frames per second, but such that only every $10^{th}$ frame is acquired at a dose (or with other acquisition parameters) that are typically utilized for anatomic visualization, such as vessel morphology. The systems and methods provided herein overcome the aforementioned drawback by utilizing high-dose frames, in some non-limiting examples, only acquiring a minimum number of high-dose frames required to ensure that diagnostic image quality is maintained for the purpose of conventional low frame rate angiography. Then, in this non-limiting example, the remaining number of images to yield a desired frame rate are acquired as low-dose frames. These low-dose frames, thus, provide contrast medium dynamics to evaluate hemodynamics, for example, such as blood velocity or flow, localization of a bleed, determining the degree of embolization.

In accordance with one aspect of the present disclosure, a system is provided for acquiring images. The system includes an imaging system configured to acquire images from the subject using ionizing radiation and a computer system. The computer system is configured to control the imaging system to deliver a series of doses of the ionizing radiation to the subject that includes at least a high dose of the ionizing radiation dose and a low dose of the ionizing radiation dose during an imaging session to acquire imaging data. The computer system is further programmed to control the imaging system to deliver more low doses of the ionizing radiation than high doses of ionizing radiation during the imaging session to acquire the imaging data to include a high frame rate of low dose data and a low frame rate of high dose data while interspersing the high doses of the ionizing radiation within the low doses of the ionizing radiation. The computer system is further configured to generate at least angiographic images of the subject and dynamic images of the subject from the imaging data.

In accordance with another aspect of the present disclosure, a method is provided for creating both angiographic images of a subject and dynamic images of the subject from imaging data acquired during an imaging acquisition. The method includes operating an imaging system to perform an imaging acquisition by delivering interspersed doses of high doses of the ionizing radiation and low doses of the ionizing radiation, wherein more low doses of the ionizing radiation are delivered than high doses of ionizing radiation during the imaging acquisition to thereby acquire the imaging data with a high frame rate of low dose data and a low frame rate of high dose data. The method also includes generating at least volumetric angiographic images of the subject and dynamic images of the subject from the imaging data.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 2A is a graphic illustration of a multi-acquisition process for acquiring both digital subtraction angiography and fluoroscopy data from a subject using different acquisition parameters.

FIG. 2B is a graphic illustration of an acquisition process for acquiring digital subtraction angiography data from a subject using high-dose irradiations.

FIG. 2C is a graphic illustration of a single interleaved process for acquiring both data for angiographic and hemodynamic images from a subject in accordance with the present disclosure at a substantially reduced contrast dose and time savings compared to the process of FIG. 2A and a substantially reduced radiation dose compared to the processes of FIG. 2B.

DETAILED DESCRIPTION

The present disclosure provides systems and methods for generating diagnostic quality angiographic images and flow kinetics or velocity at a reduced radiation dose relative to traditional imaging procedures, such as DSA. Diagnostic quality angiographic images and hemodynamics can be generated using the systems and methods of the present disclosure in a single scan, while reducing patient radiation dose and contrast media load compared to traditional imaging procedures, such as DSA.

Figure 1A:
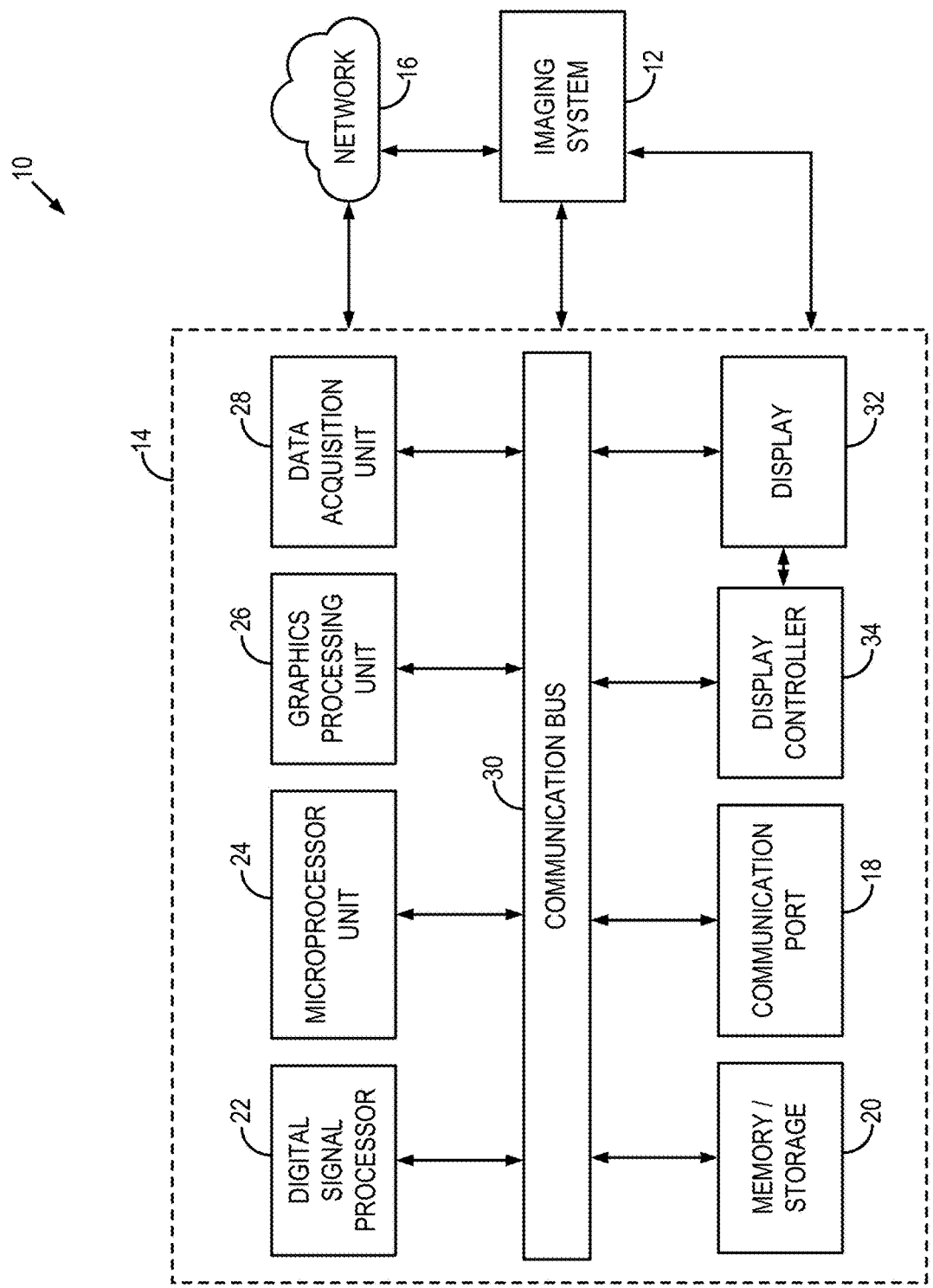
FIG. 1A is a schematic diagram of an example system in accordance with the present disclosure and that can be configured to implement the methods described herein.

Referring now to FIG. 1A, a block diagram of an example system 10 is provided that can be configured to carry out techniques, methods, and processes accordance with the present disclosure. The system may include an imaging system 12 that is coupled to a computer system 14. The coupling of the imaging system 12 to the computer system 14 may be a direct or dedicated network connection, or may be through a broad network 16, such as an intranet or the Internet.

The computer system 14 may be a workstation integrated with or separate from the medical imaging systems 12 or a variety of other medical imaging systems, including, as non-limiting examples, fluoroscopy systems, which may be coupled with or substituted by either gantry-based or C-arm computed tomography (CT) systems and the like. The CT system can be configured to utilize a fan or cone beam or other beam geometry. Relatedly, "x-ray data," "CT data," "x-ray dataset," or "CT dataset" may refer to 2D data or 3D data, or the like. As used herein "x-ray" or "CT" or "data" or "dataset" can be used in reference to any of these system, acquisition implementations, or data unless specifying otherwise.

The computer system 14 may be a workstation integrated within the medical imaging system 12 or may be a separate workstation or mobile device or computing system. To this end, the following description of particular hardware and configurations of the hardware of the example computer system 14 is for illustrative purposes. Some computer systems may have varied, combined, or different hardware configurations, and may include commercially-available computer systems or specialized computer systems.

Medical imaging data acquired by the medical imaging system 12 or other imaging system and can be provided to the computer system 14, such as over the network 16 or from a storage device. To this end, the computer system 14 may include a communications port or other input port 18 for communication with the network 16 and system coupled thereto. Also, the computer system 14 may include memory and storage capacity 20 to store and access data or images.

In some configuration, computer system 14 may include one or more processing systems or subsystems. That is, the computer system 14 may include one or more physical or virtual processors. As an example, the computer system 14 may include one or more of a digital signal processor (DSP) 22, a microprocessor unit (MPU) 24, and a graphics processing unit (GPU) 26 (or other processors, such as field programmable gate arrays (FPGAs)). If the computer system 14 is integrated into the medical imaging system, a data acquisition unit 28 may be connected directly to the above-described processor(s) 22, 24, 26 over a communications bus 30, instead of communicating acquired data or images via the network 16. As an example, the communication bus 30 can be a group of wires or wireless systems, or hardwire used for switching data between the peripherals or between any components, such as the communication buses described above.

The computer system 14 may also include or be connected to a display 32. To this end, the computer system 14 may include a display controller 34. The display 32 may be a monitor connected to the computer system 14 or maybe integrated with the computer system 14, such as in portable computers or mobile devices.

Figure 1B:
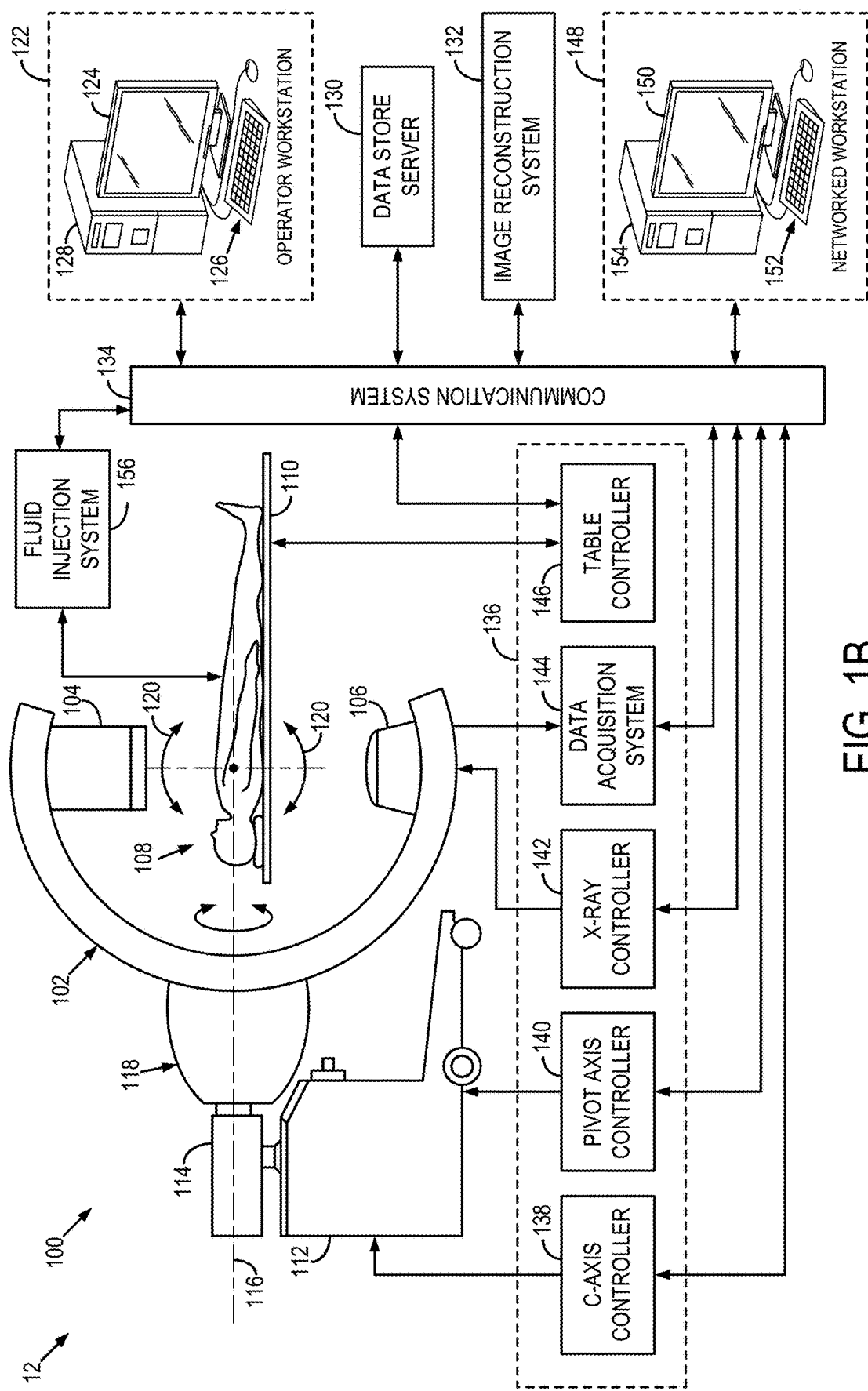
FIG. 1B is a schematic diagram of an x-ray system capable of 2D projection and/or 3D volumetric imaging that can be configured in accordance with the present disclosure.

Referring to FIG. 1B, one, non-limiting example of the imaging system 12 is provided. Specifically, in this example, an x-ray imaging system 100 is illustrated for use in accordance with some aspects of the present disclosure. However, the systems and methods provided herein are not limited to a particular structure or architecture of x-ray imaging system, including fluoroscopy or other systems.

Thus, in the non-limiting example illustrated in FIG. 1B, the imaging system 12 forms a C-arm CT imaging system 100 that includes a gantry 102 to which an x-ray source assembly 104 is coupled on one end and an x-ray detector array assembly 106 is coupled at its other end. The gantry 102 enables the x-ray source assembly 104 and detector array assembly 106 to be oriented in different positions and angles around a subject 108, such as a medical patient or an object undergoing examination, which is positioned on a table 110. When the subject 108 is a medical patient, this configuration enables a physician access to the subject 108.

The x-ray source assembly 104 includes at least one x-ray source that projects an x-ray beam, which may be a beam, fan-beam, or cone-beam of x-rays, towards the x-ray detector array assembly 106 on the opposite side of the gantry 102. The x-ray detector array assembly 106 includes at least one x-ray detector, which may include a number of x-ray detector elements. Examples of x-ray detectors that may be included in the x-ray detector array assembly 106 include flat panel detectors, such as so-called "small flat panel" detectors.

Together, the x-ray detector elements in the one or more x-ray detectors housed in the x-ray detector array assembly 106 sense the projected x-rays that pass through a subject 108. Each x-ray detector element produces an electrical signal that may represent the intensity of an impinging x-ray beam and, thus, the attenuation of the x-ray beam as it passes through the subject 108. In some configurations, each x-ray detector element is capable of counting the number of x-ray photons that impinge upon the detector. During a scan to acquire x-ray projection data, the gantry 102 and the components mounted thereon rotate about an isocenter of the C-arm x-ray imaging system 100.

The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a drive assembly 118 on its outer end. The gantry 102 is fastened to the drive assembly 118 and is coupled to a drive motor (not shown) that slides the gantry 102 to revolve it about a C-axis, as indicated by arrows 120. The pivot axis 116 and C-axis are orthogonal and intersect each other at the isocenter of the x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110. During a scan, the x-ray source and detector array are rotated about the system isocenter to acquire x-ray attenuation projection data from different angles. The imaging system 12 may include or be used with a fluid injection system 156. The fluid injection system 156 may deliver a fluid, such as a contrast agent, to the subject during the imaging acquisition The x-ray imaging system 100 also includes an operator workstation 122, which typically includes a display 124, one or more input devices 126, such as a keyboard and mouse; and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store server 130, and image reconstruction system 132 may be connected via a communication system 134, which may include any suitable network connection, whether wired, wireless, or a combination of both. As an example, the communication system 134 may include both proprietary or dedicated networks, as well as open networks, such as the internet.

The operator workstation 122 is also in communication with a control system 136 that controls operation of the x-ray imaging system 100. The control system 136 generally includes a C-axis controller 138, a pivot axis controller 140, an x-ray controller 142, a data acquisition system ("DAS") 144, and a table controller 146. The x-ray controller 142 provides power and timing signals to the x-ray source assembly 104, and the table controller 146 is operable to move the table 110 to different positions and orientations within the x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data is communicated from the DAS 144 to the data store server 130. The image reconstruction system 132 then retrieves the x-ray data from the data store server 130 and reconstructs or otherwise generates an image therefrom. The image reconstruction system 130 may include a commercially available computer processor, or may be a highly parallel computer architecture, such as a system that includes multiple-core processors and massively parallel, high-density computing devices. Optionally, image reconstruction can also be performed on the processor 128 in the operator workstation 122. Reconstructed images can then be communicated back to the data store server 130 for storage or to the operator workstation 122 to be displayed to the operator or clinician.

The x-ray imaging system 100 may also include one or more networked workstations 148. By way of example, a networked workstation 148 may include a display 150; one or more input devices 152, such as a keyboard and mouse; and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol ("TCP"), the Internet protocol ("IP"), or other known or suitable protocols.

Currently, there are no 2D x-ray imaging techniques available that allow for or utilize interleaved modulation of x-ray tube parameters for this purpose. For example, referring to FIG. 2A, a graph is provided showing timing and relative radiation dose of DSA acquisitions 200 and fluoroscopy acquisitions 202. In FIG. 2A, a higher bar corresponds to a high dose frame whereas a shorter bar is a low dose frame. Currently, if a clinician wants to acquire diagnostic-quality angiographic images and capture contrast medium dynamics, it is necessary to perform both the low frame-rate DSA acquisition 200 and the high frame-rate fluoroscopy acquisition 202. According to this common imaging process illustrated in FIG. 2A, the patient receives the sum of the radiation dose represented by both the low frame-rate DSA acquisition 200 and the high frame-rate fluoroscopy acquisition 202, and endures two scans and two contrast injections.

Referring to FIG. 2B, alternatively the fluoroscopy acquisition 202 of FIG. 2A can be eliminated by increasing the frame rate of the DSA acquisition 204 to the frame rate required to capture the hemodynamics. Unfortunately, while reducing the complexity of coordinating the operation of a DSA acquisition and a fluoroscopy acquisition, the dose of radiation received by the patient is dramatically increased. Thus, such a process is generally not performed.

Alternatively, in accordance with one non-limiting aspect of the disclosure, x-ray tube parameters (kV, mA, ms, and the like) may be controlled or modulated on a frame-by-frame basis during acquisition of a sequence of x-ray images to produce an interleaved sequence of high and low dose frames. For example, one non-limiting example of a process in accordance with the present disclosure is illustrated in FIG. 2C. In the non-limiting example provided in FIG. 2C, an interleaved acquisition 206 is provided that combines both low-dose and high-dose image frames into a single acquisition. Though illustrated as a consistent number of high and low dose frame rates, the balance between the high frame rate of low dose data and the low frame rate of high dose data may be varied. Thus, a single injection of contrast medium can be utilized, which is a substantial improvement over the process of FIG. 2A, and at a substantially lower radiation dose than possible with the process of FIG. 2B. That is, compared to the process of FIG. 2A, the radiation dose level is maintained and the contrast medium dose and imaging time is reduced. Compared to the process of FIG. 2B, the radiation dose is substantially reduced.

Figure 2D:
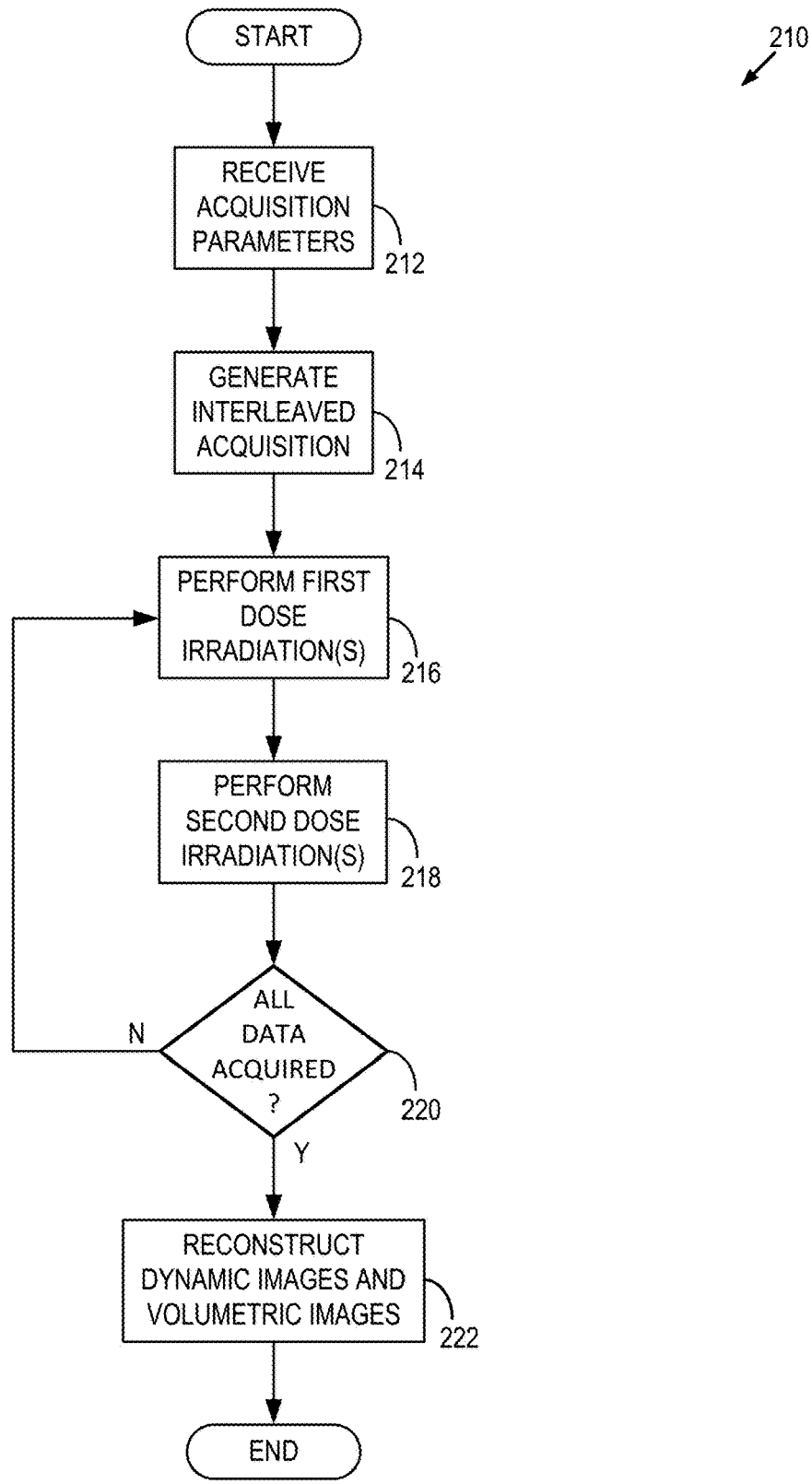
FIG. 2D is a flow chart setting forth some non-limiting example steps of a method for acquiring both data for angiographic and hemodynamic images from a subject in accordance with the present disclosure.

Thus, referring to FIG. 2D, a process 210 implementing the above-described imaging strategy can include receiving acquisition parameters at process block 212. In particular, a clinician may select a desired frame rate for the dynamic/hemodynamic images and/or may select particular operational parameters, such as the voltage, tube current, or pulse width to be used during imaging, either for the low dose irradiations and/or the high dose irradiations, or a combination thereof. At process block 214, this information is then used to plan an interleaved or varying acquisition designed, as a non-limiting example, to acquire angiographic images of a subject and dynamic images of the subject from imaging data acquired during the interleaved imaging acquisition.

At process block, 216, the interleaved or varying imaging process begins. As will be described, the present non-limiting example describes two different, or discrete levels of modulation in an "interleaving" process. However, a "varying" or otherwise "modulating" process may be used where multiple different levels of radiation may be used. For example, instead of "high" and "low" levels, a modulating the dose may be used. For example, a sinusoidal modulation or other continuous modulation may be used to further dose reduction. Thus, the present non-limiting example is just one particular implementation that may be used.

More particularly, a first dose or sequence of doses is performed at process block 216 followed by a second dose or sequence of doses at process block 218. These process blocks are repeated at decision block 220 until all of the desired data is acquired. In one non-limiting example, the imaging acquisition is performed by delivering interspersed doses of high doses of the ionizing radiation and low doses of the ionizing radiation, wherein more low doses of the ionizing radiation are delivered than high doses of ionizing radiation during the imaging acquisition to thereby acquire the imaging data with a high frame rate of low dose data and a low frame rate of high dose data. That is, the imaging acquisition may include delivering interspersed doses of high doses of the ionizing radiation and low doses of the ionizing radiation, wherein more low doses of the ionizing radiation are delivered than high doses of ionizing radiation during the imaging acquisition to thereby acquire the imaging data with a high frame rate of low dose data and a low frame rate of high dose data. The specific balance of more low doses of the ionizing radiation being delivered than high doses of ionizing radiation during the imaging acquisition may be varied, for example, with each repetition of decision block 220, or at particular or selected intervals in time or acquisitions.

Once all the data is acquired, at process block 222, images of the subject and dynamic images of the subject are reconstructed from the imaging data. The images can be volumetric, but need not be so. For example, this step may include using the low dose data to produce the dynamic images showing contrast medium dynamics in the subject and using the high dose data to produce digital subtraction angiography (DSA) images of the subject. The DSA images may include three-dimensional volumetric images. The dynamic images may be reconstructed to produce a series of images at 30 frames per second. For quantitative DSA (qDSA) blood velocity computations, a time series of 2D-DSA images are acquired, which forms a "dynamic image sequence" but it doesn't require "reconstruction" in the sense of, for example, filtered backprojection CT reconstruction. In other situations, if interleaving is performed with respect to a 4D-DSA acquisition, 4D-DSA reconstruction is performed to generate the "dynamic image sequence". In any case, the acquisition of data at process blocks 216 and 218 may be performed to acquire imaging data. In one non-limiting example, imaging data may be acquired at 30 frames per second, wherein one of every third, sixth, or tenth frame is acquired using the high dose of ionizing radiation.

The systems and methods of the present disclosure are particularly useful in a variety of different clinical settings. In one non-limiting example, an interleaved sequence such as illustrated in FIG. 2C may be designed such that the overall frame rate is desirably high for a given clinical purpose, such as 30 frames per second for tracking hemodynamics, but such that the high-dose frames are generated at a low rate and the remaining frames are low dose. In one non-limiting example, the overall acquisition may acquire 30 frames per second, but such that only every $10^{th}$ frame is acquired at a dose (or with other acquisition parameters) that are typically utilized for anatomic visualization, such as vessel morphology. A different number may also be used, such as every $2^{nd}$, $3^{rd}$, $4^{th}$, $5^{th}$, $6^{th}$, $7^{th}$, $8^{th}$, $9^{th}$ $10^{th}$, or other number of frame. The systems and methods provided herein overcome the aforementioned drawback by utilizing high-dose frames, in some non-limiting examples, only acquiring a reduced or minimum number of high-dose frames required to ensure that diagnostic image quality is maintained for the purpose of conventional low frame rate angiography. Then, in this non-limiting example, the remaining number of images to yield a desired frame rate are acquired as low-dose frames. These low-dose frames, thus, provide contrast medium dynamics to evaluate hemodynamics, for example, such as blood velocity or flow, localization of a bleed, determining the degree of embolization. Then, in this non-limiting example, the remaining number of images to yield a desired frame rate are acquired as low-dose frames. These low-dose frames, thus, provide contrast medium dynamics to evaluate hemodynamics, for example, such as blood velocity or flow, localization of a bleed, determining the degree of embolization.

Non-Limiting Examples

The systems and methods provided herein have been evaluated in a flow phantom study using a straight ¼ inch tube embedded in tissue mimicking material, a pulsatile flow pump, and a C-arm imaging system. The flow pump was set to mimic a heart rate of 60 bpm with an average velocity of 50 cm/s during contrast media injection. Imaging was performed on the Siemens Artis zee interventional x-ray angiography system in the UW Image Guided Interventions Lab. The x-ray system was equipped with software that allowed for frame-by-frame manual specification of x-ray tube parameters (kV, mA, ms). This capability was used to program interleaved high/low dose x-ray sequences in the flow phantom study.

Initially, DSA and CINE imaging series were acquired from the phantom to determine realistic x-ray tube parameters for non-interleaved imaging. Tube parameters for the low-dose frames were then calculated by exploiting the ability to modulate the x-ray pulse width (ms) while keeping other parameters (kV, mA) fixed. In the research prototype, the range of pulse width varied form 10 ms to 3.2 ms. Thus, the low dose frames were acquired at 32% of the high-dose level. Image grayscale values were divided by their mAs (ms and mA product per frame) to have a consistent image intensity level throughout the interleaved sequence. Three interleaved imaging series were acquired, each with a total frame rate of 30 frames per second and a high dose frame frequency of 3, 5, and 10 frames per second. These interleaved techniques resulted in 39%, 43%, and 55% of the dose rate of a conventional 30 frames per second DSA scan.

It is noted that other methods can be used to reduce dose further, such as kV modulation and mA modulation, but were not used in this one, non-limiting example.

Figure 3:
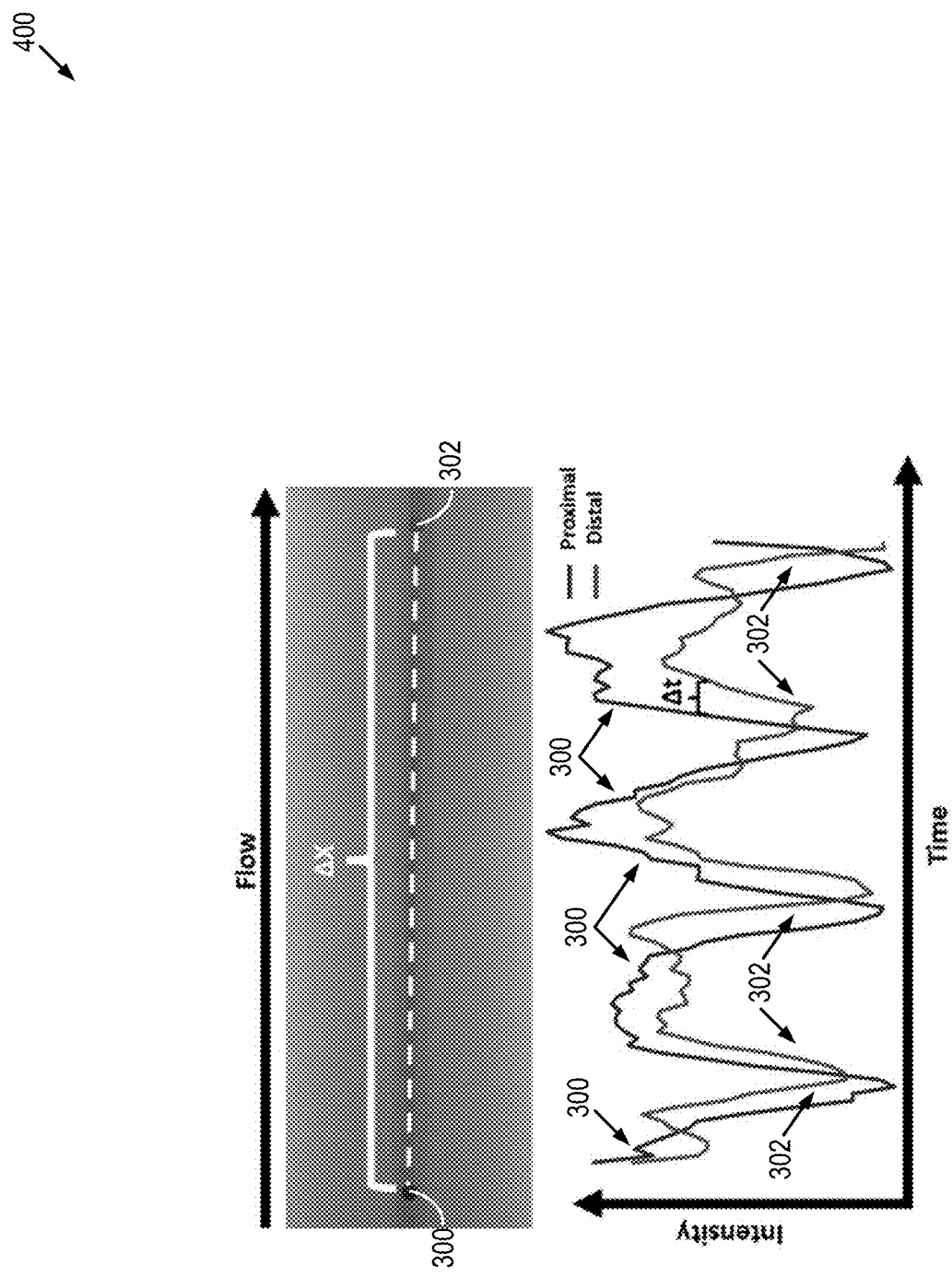
FIG. 3 is a diagram of an example of data acquired using quantitative digital subtraction angiography blood velocity in a study in accordance with the present disclosure.

FIG. 3 provides an example image flowing flow direction through the phantom over a distance ΔX from a proximal location 300 to a distal location 302. The two measured curves in FIG. 3 can be used to determine the temporal shift, ΔT, and the combination of ΔX and ΔT can then be used to compute the velocity. In particular, measuring ΔX and ΔT for two points yields velocity as ΔX/ΔT because, of course, velocity is the derivative of position. However, when performing qDSA, it can be advantageous to utilize a collection of different pairs of points along a vessel segment to create an average velocity. Blood velocities were computed using a quantitative DSA (qDSA) approach that tracks contrast medium along a vessel centerline extending from the proximal location 300 to the distal location 302. This was used to assess the conservation of the contrast medium dynamics for a full high dose scan versus the interleaved technique described herein.

Figure 4:
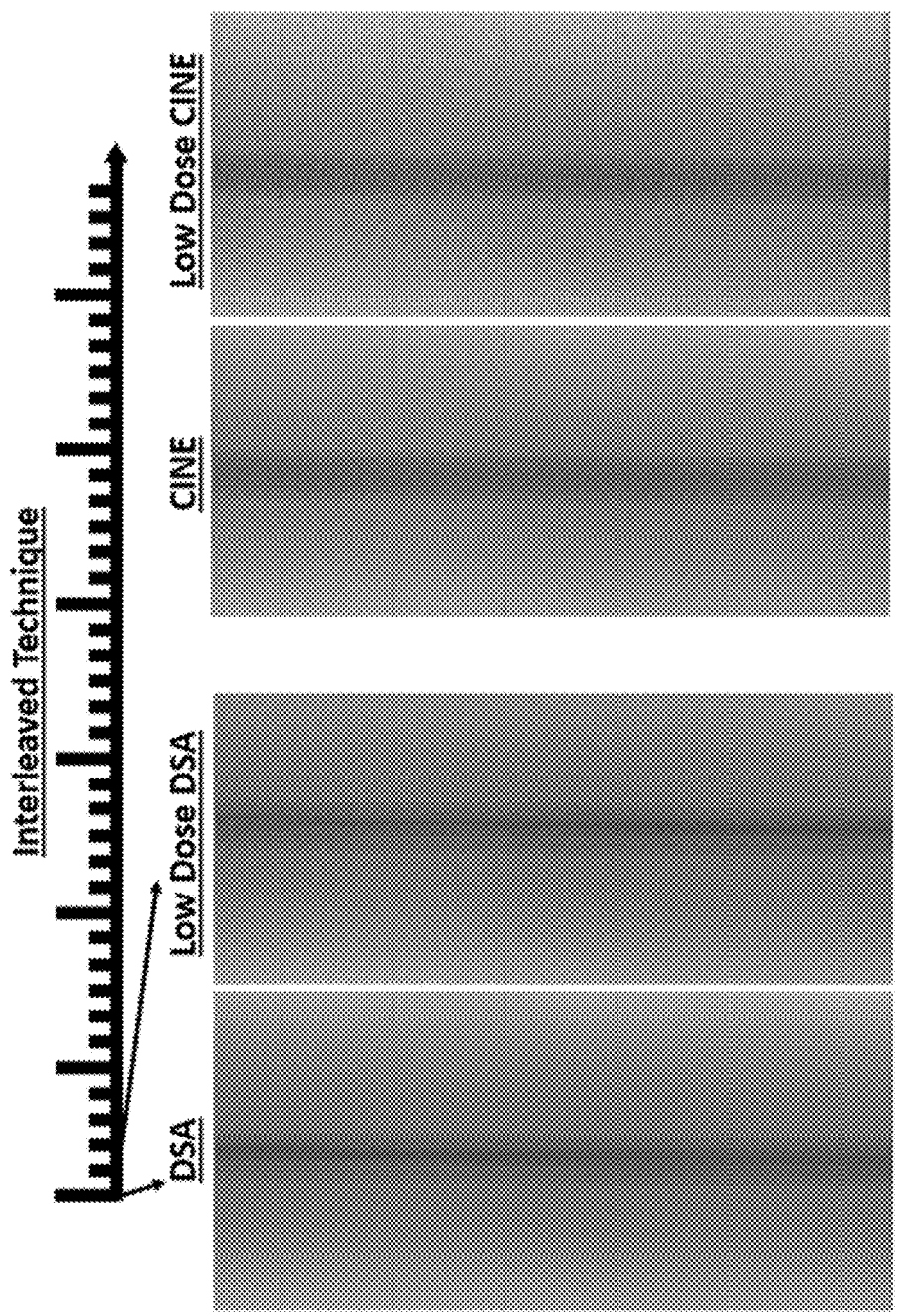
FIG. 4 is a set of raw images for two example interleaved sequences acquired in a study in accordance with the present disclosure.

As expected from basic x-ray physics, images acquired with higher dose had lower image noise (relative to iodine signal), and images acquired at a lower dose had higher image noise. Specifically, FIG. 4 shows relative image noise levels for two example interleaved sequences. That is, FIG. 4 shows the sequence produced using DSA-quality for the high-dose frames next two the sequence produced using CINE-quality for the high-dose frames. In both cases the low-dose frame is generated using 32% of the high dose value. As expected, the image noise increases when dose is reduced.

Figure 5:
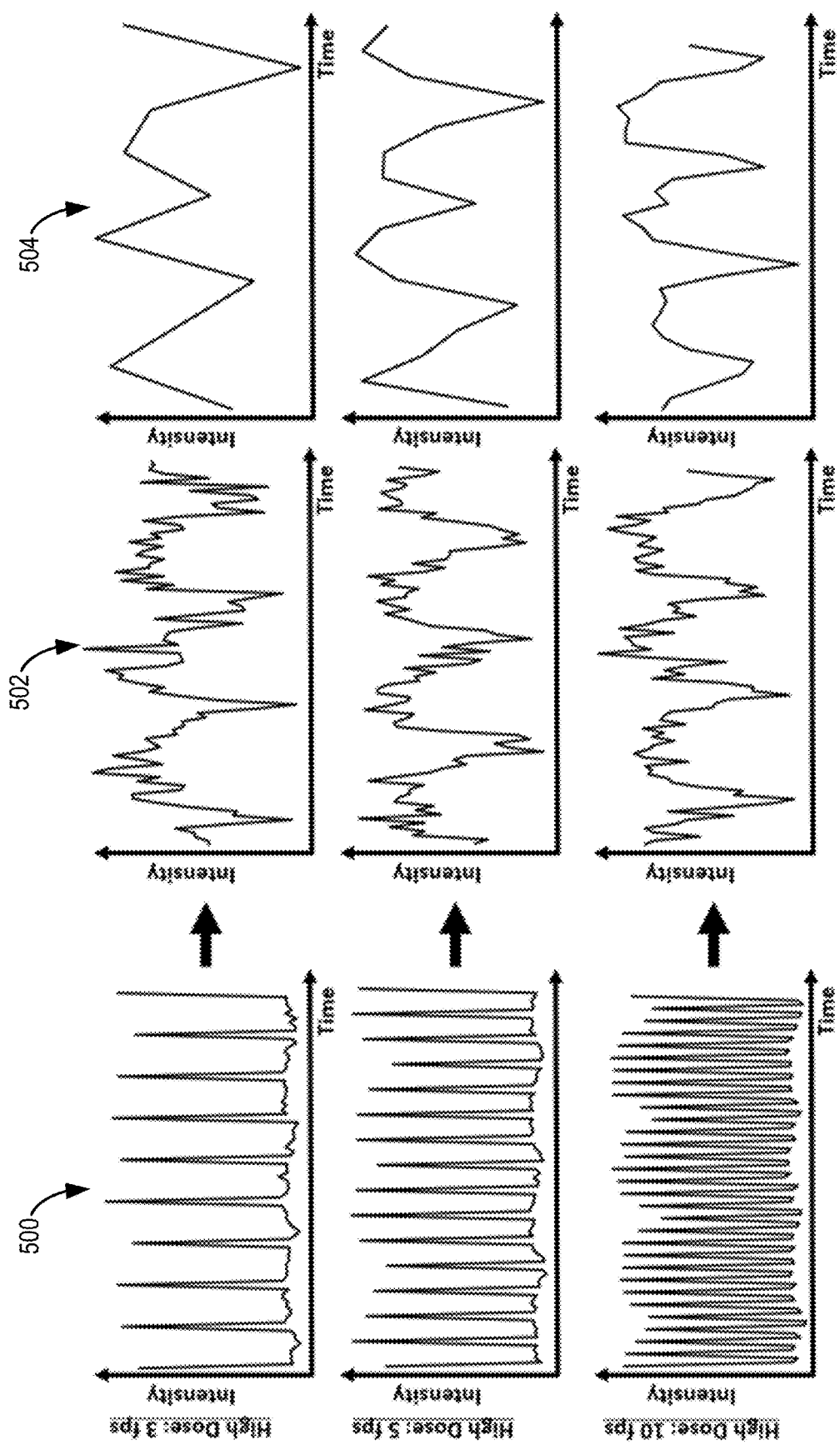
FIG. 5 is a set of graphs showing the effectiveness of high-dose frames and low-dose frames for different purposes, such as capturing periodic oscillations in image contrast to derive blood velocity.

To examine the fidelity of the contrast medium dynamics in an interleaved image sequence, time-attenuation curves were extracted from a point along the vessel centerline. As shown in FIG. 5 in the left column 500, the raw image intensity primarily reflects the overall dose level used to acquire the resulting image. That is, the left column of FIG. 5 shows raw image intensity at a point inside the vessel for three different interleaved sequences acquired at 30 frame/s. The high dose frames are acquired at 3 frame/s (e.g., every $10^{th}$ frame), 5 frame/s (e.g., every $6^{th}$ frame), and 10 frame/s (e.g., every $3^{rd}$ frame) in this example. The spikes in intensity are caused by variation in mAs/frame.

However, after normalizing the raw intensity by mAs per frame 502, a periodic signal can be seen. This is the periodic oscillation in contrast medium density that is tracked by the qDSA algorithm to estimate blood velocity. When the time-attenuation data is viewed in terms of the high-dose frames only 504, there is a loss in fidelity of the contrast dynamics. The loss in fidelity is caused by the relatively low temporal sampling associated with the high dose frames.

The impact of low frame rate is further quantified in Table 1.

| Technique | Velocity [cm/s] (30 frame/s imaging) | Velocity [cm/s] using only high dose frames (reduced frame rate) |
|---|---|---|
| All frames @ DSA dose | 110, 108, 111 | |
| Every $3^{rd}$ frame @ DSA dose | 110, 110, 112 | 94, 99, 104 |
| Every $6^{th}$ frame @ DSA dose | 111, 111, 111 | 121, 104, 104 |
| Every $10^{th}$ frame @ DSA dose | 110, 107, 111 | 239, 188, 295 |
| All frames @ Cine dose | 129, 128, 127 | |

| Technique | Velocity [cm/s] (30 frame/s imaging) | Velocity [cm/s] using only high dose frames (reduced frame rate) |
| --- | --- | --- |
| Every $3^{rd}$ frame @ Cine dose | 133, 136, 125 | 132, 134, 108 |
| Every $6^{th}$ frame @ Cine dose | 129, 132, 129 | 224, 240, 193 |
| Every $10^{th}$ frame @ Cine dose | 129, 133, 129 | 323, 191, 611 |

That is, Table 1 compares blood velocity calculations obtained with 30 frame/s low-dose interleaved imaging versus conventional 30 frame/s high-dose imaging (either DSA or CINE image quality). In the center column, data is provided for 30 frame/s imaging, which shows that there was strong agreement between results obtained between the low-dose interleaved technique (every $3^{rd}$, $6^{th}$, and $10^{th}$ frame) and the high-dose all-DSA technique (All frames). In the right column, to demonstrate that 30 frame/s imaging is needed in this experiment, qDSA was also attempted using only the high dose frames from the interleaved technique. When the frame rate was effectively reduced in this manner, there was poor agreement with the 30 frame/s DSA gold standard. In the bottom of the table, similar results were obtained when the gold standard was high-dose CINE quality.

Thus, a strong agreement was demonstrated between the gold standard high-dose acquisitions and all the tested interleaved techniques. In contrast, when using only the high-dose frames of an interleaved sequence, and thus a low frame rate (i.e. mimicking a clinical low frame rate DSA or CINE protocol) there were large disagreements between computed velocity and the gold standard. The results indicate that 30 frame/s imaging may be desirable for blood velocity analysis, and radiation dose reduction can be obtained using the interleaved technique.

By using the interleaved imaging technique, it is feasible to capture diagnostic quality angiographic images and contrast medium dynamics from a single imaging series. This would allow for the potential of quantitative blood velocity computations, bleed localization and embolization evaluation during interventional radiology procedures while preserving the vessel visibility expected of conventional angiography. Interleaved imaging could eliminate alternative approaches that require either multiple imaging acquisitions or higher radiation dose rates. It promises to facilitate the translation of DSA-based quantitative blood velocity measurements into the clinic by reducing the required patient dose and injected contrast medium dose. Future research is warranted to optimize dose reduction, noise reduction, and motion artifacts, but it is clear this technique works and could have a direct impact on 2D x-ray transmission imaging in interventional radiology.

Thus, the interleaved imaging technique provided herein, allows for the clinical acquisition of conventional low-frame rate diagnostic-quality angiographic images and high-frame rate contrast medium dynamics in a single image series, with reduced radiation dose relative to high-frame rate diagnostic-quality angiography. The technique supports new DSA-based quantitative blood velocity computations, while managing vessel visibility, radiation dose, and contrast medium dose.

The systems and methods described herein have wide clinical application. For example, liver embolization is an effective, minimally invasive treatment option for patients with intermediate or advanced liver cancer. However, angiographic monitoring of residual blood flow to treated tumors is critical to the success of the procedure. The systems and methods provided herein provide a quantitative metric of flow to guide performance of the embolization, as there is a fine line between too much and too little in vessel embolization. Similarly, the systems and methods provided herein find ready application in cardiac and neuro angiography to quantitate blood flow in vessels, including for aneurism treatment and any of a variety of interventional procedures that benefit from high-resolution and functional, such as hemodynamic, images.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for acquiring images, the system comprising:
an imaging system configured to acquire images from a subject using ionizing radiation; and
a computer system configured to control the imaging system to:
deliver a series of doses of the ionizing radiation to the subject that includes at least a high dose of the ionizing radiation dose and a low dose of the ionizing radiation dose during an imaging session to acquire imaging data;
deliver more low doses of the ionizing radiation than high doses of ionizing radiation during the imaging session to acquire the imaging data to include a high frame rate of low dose data and a low frame rate of high dose data while interspersing the high doses of the ionizing radiation within the low doses of the ionizing radiation; and
generate at least angiographic images showing vessels of the subject using the high dose data and dynamic images of the subject showing contrast medium dynamics in the subject using the low dose data;
wherein the series of doses of the ionizing radiation delivers a total dose that is less than required to produce the at least the angiographic images of the subject and the dynamic images of the subject from the imaging data using two non-interleaved acquisition processes.

2. The system of claim 1 wherein computer system is further configured to produce digital subtraction angiography (DSA) images of the subject as the angiographic images.

3. The system of claim 2 wherein the dynamic images are generated to produce a series of images at 30 frames per second.

4. The system of claim 2 wherein the DSA images include three-dimensional volumetric images.

5. The system of claim 1 wherein the computer system is further programmed to acquire the imaging data at 30 frames per second, wherein one of every third, sixth, or tenth frame is acquired using the high dose of ionizing radiation.

6. The system of claim 1 wherein the computer system is further programmed to adjust one of a voltage, tube current, or pulse width of the ionizing radiation dose to create the high dose and the low dose of the ionizing radiation.

7. The system of claim 1 wherein the imaging system includes a computed tomography imaging system.

8. The system of claim 7 wherein the computed tomography system is a c-arm system.

9. The system of claim 1 wherein the computer system is configured to control the imaging system to vary a balance between the high frame rate of low dose data and the low frame rate of high dose data.

10. A method for creating both angiographic images of a subject and dynamic images of the subject from imaging data acquired during an imaging acquisition, the method including steps comprising:
   operating an imaging system to perform the imaging acquisition by delivering interspersed doses of high doses of ionizing radiation and low doses of ionizing radiation, wherein more of the low doses of the ionizing radiation are delivered than the high doses of ionizing radiation during the imaging acquisition to thereby acquire the imaging data with a high frame rate of low dose data and a low frame rate of high dose data; and
   generating at least volumetric angiographic images showing vessels of the subject us ing the high dose data and dynamic images of the subject showing contrast medium dynamics in the subject using the low dose data;
   wherein the interspersed doses delivers a total dose that is less than required to produce the at least the volumetric angiographic images of the subject and the dynamic images of the subject from the imaging data using two non-interleaved acquisition processes.

11. The method of claim 10 further comprising producing digital subtraction angiography (DSA) images of the subject as the volumetric angiographic images.

12. The method of claim 11 further comprising generating the dynamic images to produce a series of images at 30 frames per second.

13. The method of claim 11 further comprising generating the DSA images as three-dimensional volumetric images.

14. The method of claim 10 further comprising acquiring the imaging data at 30 frames per second, wherein one of every third, sixth, or tenth frame is acquired using the high dose of ionizing radiation.

15. The method of claim 10 further comprising adjusting one of a voltage, tube current, or pulse width of the ionizing radiation dose to create the high dose and the low dose of the ionizing radiation.

16. The method of claim 10 wherein the imaging system includes a computed tomography imaging system.

17. The method of claim 16 wherein the computed tomography system is a c-arm system.

18. The method of claim 10 further comprising varying a balance between the high frame rate of low dose data and the low frame rate of high dose data.

* * * * *

UNITED STATES PATENT AND TRADEMARK OFFICE
CERTIFICATE OF CORRECTION

PATENT NO. : 12,133,754 B2
APPLICATION NO. : 17/721697
DATED : November 5, 2024
INVENTOR(S) : Michael Speidel et al.

It is certified that error appears in the above-identified patent and that said Letters Patent is hereby corrected as shown below:

In the Claims

Claim 10, Column 13, Line 17, "us ing" should be --using--.

Signed and Sealed this
Thirty-first Day of December, 2024

Derrick Brent
*Acting Director of the United States Patent and Trademark Office*